(12) United States Patent
Banes et al.

(10) Patent No.: US 8,288,511 B2
(45) Date of Patent: Oct. 16, 2012

(54) NUCLEAR TARGETING SEQUENCE

(75) Inventors: Albert J. Banes, Hillsborough, NC (US); Jie Qi, Chapel Hill, NC (US)

(73) Assignee: Medtrain Technologies, LLC, Hillsborough, NC (US)

( * ) Notice: Subject to any disclaimer, the term of this patent is extended or adjusted under 35 U.S.C. 154(b) by 472 days.

(21) Appl. No.: 12/464,619

(22) Filed: May 12, 2009

(65) Prior Publication Data

US 2009/0275136 A1    Nov. 5, 2009

Related U.S. Application Data

(62) Division of application No. 11/293,891, filed on Dec. 2, 2005, now Pat. No. 7,531,624.

(60) Provisional application No. 60/633,243, filed on Dec. 3, 2004.

(51) Int. Cl.
A61K 38/04 (2006.01)
(52) U.S. Cl. ........................................ 530/329; 435/325
(58) Field of Classification Search ........................ None
See application file for complete search history.

(56) References Cited

U.S. PATENT DOCUMENTS 6,623,966 B1    9/2003   Lane

FOREIGN PATENT DOCUMENTS

| WO | 0118216 A2 | 3/2001 |
|---|---|---|
| WO | 2004076614 A2 | 9/2004 |

OTHER PUBLICATIONS

Verma et al. (Nature 1997, 389: 239-242).*
Amalfitano et al. (Current Gene Therapy 2002, 2: 111-133).*
Nagasaki et al. (Bioconjugate Chem., Mar. 2003, vol. 14, pp. 282-286, cited on IDS filed Jul. 2009.*
Dingwall et al., "Nuclear Targeting Sequences—a Consensus?", TIBS, vol. 16, 1991, 478-481.
Erich A. Nigg, "Nucleocytoplasmic Transport: Signals, Mechanisms and Regulation", Nature, 1997, vol. 386, 779-787.
Dirk Gorlich, "Transport into and out of the Cell Nucleus", Medal Review, 1998, vol. 17, No. 10, 2721-2727.
Victoria W. Pollard et al., "The HIV-1 Rev Protein", Annu. Rev. Microbiol., 1998, vol. 52, 491-532.
Matthias Dobbelstein et al., "Nuclear Export of the E1B 55-kDa and E4 34-kDa Adenoviral Oncoproteins Mediated by a Rev-Like Signal Sequence", The EMBO Journal, 1997, vol. 16, No. 14, 4276-4284.
Katharine S. Ullman et al., "Nuclear Export Receptors: From Importin to Exportin", Cell, 1997, vol. 90, 967-970.
Benjamin Guralnick et al., "Transport of DNA into the Nuclei of *Xenopus oocytes* by a Modified VirE2 Protein of *Agrobacterium*", The Plant Cell, 1996, vol. 8, 363-373.
Marguerite J. Varagona et al., "Monocot Regulatory Protein Opaque-2 is Localized in the Nucleus of Maize Endosperm and Transformed Tobacco Plants", The Plant Cell, 1991, vol. 3, 105-113.

W. Matthew Michael et al., "A Nuclear Export Signal in hnRNP A1: A Signal-Mediated, Temperature-Dependent Nuclear Protein Export Pathway", Cell, 1995, vol. 83, 415-422.
Batool Ossareh-Nazari et al., "Evidence for a Role of CRM1 in Signal-Mediated Nuclear Protein Export", Science, 1997, vol. 278, 141-144.
Kenta Nakai et al., "PSORT: A Program for Dectecting Sorting Signals in Proteins and Predicting their Subcellular Localization", TIBS, 1999, 24-25.
Abigail S. Mcelhinny et al., "Muscle-Specific RING Finger-1 Interacts with Titin to Regulate Sarcomeric M-Line and Thick Filament Structure and May Have Nuclear Functions Via Its Interaction with Glucocorticoid Modulatory Element Binding Protein-1.", The Journal of Cell Biology, 2002, vol. 157, No. 1, 125-136.
W. Glen Pyle et al., "At the Crossroads of Myocardial Signaling: The Role of Z-Discs in Intracellular Signaling and Cardiac Function", Circulation Research, 2004, vol. 94, 296-305.
Joseph W. Sanger et al., "Fishing Out Proteins That Bind to Titin", The Journal of Cell Biology, 2001, vol. 154, No. 1, 21-24.
Edward W. Harhaj et al., "Regulation of RelA Subcellular Localization by a Putative Nuclear Export Signal and p50", Molecular and Cellular Biology, 1999, 7088-7095.
W. Matthew Michael et al., "The K Nuclear Shuttling Domain: A Novel Signal for Nuclear Import and Nuclear Export in the hnRNP K Protein", The EMBO Journal, 1997, vol. 16, No. 12, 3587-3598.
Atsushi Wada, et al., "Nuclear Export of Actin: A Novel Mechanism Regulating the Subcellular Localization of a Major Cytoskeletal Protein", The EMBO Journal, 1998, vol. 17, No. 6, 1635-1641.
Jiangyu Zhu et al., "NF-AT Activation Requires Suppression of Crm1-Dependent Export by Calcineurin, Department of Cell Biology", Harvard Medical School, published by Macmillan Magazines Ltd, 1999, Nature, vol. 398, 256-260.
Stephan Lang et al., "The Kinase Domain of Titin Controls Muscle Gene Expression and Protein Turnover", Science, 2005, vol. 308, 1599-1603.
Rajesh Nair et al., "NLSdb: Database of Nuclear Localization Signals", Nucleic Acids Research, 2003, vol. 31, No. 1, 397-399.
Gad Shaulsky et al., "Nuclear Accumulation of p53 Protein Is Mediated by Several Nuclear Localization Signals and Plays a Role in Tumorigenesis", Molecular and Cellular Biology, 1990, 6565-6577.
Junona Moroianu, "Nuclear Import and Export Pathways", Journal of Cellular Biochemistry Supplements, 1999, vol. 32/33, 76-83.

(Continued)

*Primary Examiner* — Laura B Goddard
*Assistant Examiner* — Meera Natarajan
(74) *Attorney, Agent, or Firm* — The Webb Law Firm

(57) ABSTRACT

The present provides nuclear localization signaling (NLS) sequences derived from titin, comprised of amino acids 181-220: SVGRATSTAE LLVQGEEEVP AKKTKTIVST AQIS-ESRQTR and fragments thereof, such as amino acids 193-208: VQGEEEVP AKKTKTIV; amino acids 199-208: VPAKKTKTIV; and amino acids 200-206: PAKKTKT. The NLS sequences can be linked to agents, such as peptides, proteins or nucleotides, for transporting the agents into the nucleus of cells, and the NLS-agent complex can be further linked to antibodies or ligands for specific binding to cells. Also provided is a method for constructing cDNAs comprising combining a NLS sequence with a nucleic acid sequence for a target protein for expression and entry of the target protein into the nucleus of cells, which then can perform specific functions therein.

7 Claims, 5 Drawing Sheets

OTHER PUBLICATIONS

Zhan Xiao et al., "A Distinct Nuclear Localization Signal in the N Terminus of Smad 3 Determines its Ligand-Induced Nuclear Translocation", PNAS, 2000, vol. 97, No. 14, 7853-7858.

Felix M. Munkonge et al., "Emerging Significance of Plasmid DNA Nuclear Import in Gene Therapy", Advanced Drug Delivery Reviews, 2003, vol. 55, 749-760.

Cynthia J. Delong et al., "Nuclear Localization of Enzymatically Active Green Fluorescent Protein-CTP: Phosphocholine Cytidylyltransferase α Fusion Protein Is Independent of Cell Cycle Conditions and Cell Types", The Journal of Biological Chemistry, 2000, vol. 275, No. 41, 32325-32330.

Daniel Christophe et al., "Nuclear Targeting of Proteins: How Many Different Signals?", Cellular Signalling, 2000, vol. 12, 337-341.

Raymond R.R. Rowland et al., "Nucleolar-Cytoplasmic Shuttling of PRRSV Nucleocapsid Protein: A Simple Case of Molecular Mimicry or the Complex Regulation by Nuclear Import, Nucleolar Localization and Nuclear Export Signal Sequences", Virus Research, 2003, vol. 95, 23-33.

Carl Feldherr et al., "Stimulation of Nuclear Import by Simian Virus 40-Transformed Cell Extracts Is Dependent on Protein Kinase Activity", Molecular and Cellular Biology, 1995, vol. 15, No. 12, 7043-7049.

Beate Reichart et al., "Expression and Localization of Nuclear Proteins in Autosomal-Dominant Emery-Dreifuss Muscular Dystrophy with LMNA R377H Mutation", BMC Cell Biology, 2004, vol. 5, No. 12, 1-16.

Eric Hebert, "Improvement of Exogenous DNA Nuclear Importation by Nuclear Localization Signal-Bearing Vectors: A Promising Way for Non-Viral Gene Therapy?", Biology of the Cell, 2003, vol. 95, 59-68.

Roman P. Wernyj et al., "Multiple Antibodies to Titin Immunoreact with AHNAK and Localize to the Mitotic Spindle Machinery", Cell Motility and the Cytoskeleton, 2001, vol. 50, 101-113.

Virginie Escriou et al., "NLS Bioconjugates for Targeting Therapeutic Genes to the Nucleus", Advanced Drug Delivery Reviews, 2003, vol. 55, 295-306.

Van Der AA et al.; "An NLS Peptide Covalently Linked to Linear DNA Does Not Enhance Transfection Efficiency of Cationic Polymer Based Gene Delivery Systems", Journal of Gene Medicine, Oct. 2004, vol. 7, 208-217.

Seamon et al., "Inserting a Nuclear Targeting Signal Into a Replication-Competent Moloney Murine Leukemia Virus Affects Viral Export and is not Sufficient for Cell Cycle-Independent Infection", Journal of Virology, 2002, vol. 76(16), 8475-8484 (Abstract only).

Nagasaki et al., "Can Nuclear Localization Signals Enhance Nuclear Localization of Plasmid DNA?", Biconjugate Chemistry, Mar. 2003, vol. 14(2), 282-286.

Mathias Gautel et al., "The Central Z-Disk Region of Titin is Assembled From a Novel Repeat in Variable Copy Numbers", Journal of Cell Science, 1996, vol. 109, 2747-2754.

Albert J. Banes et al., "Mechanical Load Stimulates Expression of Novel Genes in Vivo and in Vitro in Avian Flexor Tendon Cells", Journal of the OsteoArthritis Research Society International, 1999, vol. 7, 141-153.

Kuan Wang et al., "Regulation of Skeletal Muscle Stiffness and Elasticity by Titin Isoforms: A Test of the Segmental Extension Model of Resting Tension", Proc. Natl. Acad. Sci. USA, 1991, vol. 88, 7101-7105.

Kenta Nakai et al., "PSORT: A Program for Detecting Sorting Signals in Proteins and Predicting their Subcellular Localization", TIBS, 1999, 24-25.

Jacqueline Robbins et al., "Two Interdependent Basic Domains in Nucleoplasmin Nuclear Targeting Sequence: Identification of a Class of Bipartite Nuclear Targeting Sequence", Cell, 1991, vol. 64, 615-623.

Tanja La Cour et al., "Analysis and Prediction of Leucine-Rich Nuclear Export Signals, Protein Engineering, Design & Selection", 2004, vol. 17, No. 6, 527-536.

Cristina Machado et al., D-TITIN: "A Giant Protein with Dual Roles in Chromosomes and Muscles", The Journal of Cell Biology, 2000, vol. 151, No. 3, 639-651.

Marie-Louise Bang et al., "The Complete Gene Sequence of Titin, Expression of an Unusual ≈700-kDa Titin Isoform, and Its Interaction with Obscurin Identify a Novel Z-Line to I-Band Linking System", Circulation Research, 2001, 1065-1072.

Stephen A. Adam et al., "Cytosolic Proteins that Specifically Bind Nuclear Location Signals Are Receptors for Nuclear Import", Cell, 1991, vol. 66, 837-847.

Naoko Imamoto et al., "In Vivo Evidence for Involvement of a 58 kDa Component of Nuclear Pore-Targeting Complex in Nuclear Protein Import", The EMBO Journal, 1995, vol. 14, No. 15, 3617-3626.

Carol C Gregorio et al., "Muscle Assembly: A Titanic Achievement?", Current Opinion in Cell Biology, 1999, vol. 11, 18-25.

* cited by examiner

SEQUENCE LISTING

<160> NUMBER OF SEQ ID NOS: 38

<210> SEQ ID NO 1
<211> LENGTH: 40
<212> TYPE: PRT
<213> ORGANISM: Homo sapiens

<400> SEQUENCE: 1

Ser Val Gly Arg Ala Thr Ser Thr Ala Glu Leu Leu Val Gln Gly Glu
1               5                   10                  15

Glu Glu Val Pro Ala Lys Lys Thr Lys Thr Ile Val Ser Thr Ala Gln
            20                  25                  30

Ile Ser Glu Ser Arg Gln Thr Arg
        35                  40

<210> SEQ ID NO 2
<211> LENGTH: 16
<212> TYPE: PRT
<213> ORGANISM: Homo sapiens

<400> SEQUENCE: 2

Val Gln Gly Glu Glu Glu Val Pro Ala Lys Lys Thr Lys Thr Ile Val
1               5                   10                  15

<210> SEQ ID NO 3
<211> LENGTH: 10
<212> TYPE: PRT
<213> ORGANISM: Homo sapiens

<400> SEQUENCE: 3

Val Pro Ala Lys Lys Thr Lys Thr Ile Val
1               5                   10

<210> SEQ ID NO 4
<211> LENGTH: 7
<212> TYPE: PRT
<213> ORGANISM: Homo sapiens

<400> SEQUENCE: 4

Pro Ala Lys Lys Thr Lys Thr
1               5

<210> SEQ ID NO 5
<211> LENGTH: 36
<212> TYPE: DNA
<213> ORGANISM: Homo sapiens

<400> SEQUENCE: 5
aaaaggatcc ctatgacaac tcaagcaccg acgttt        36

```
<210> SEQ ID NO 6
<211> LENGTH: 39
<212> TYPE: DNA
<213> ORGANISM: Homo sapiens

<400> SEQUENCE: 6
aaaactcgag aattactgtg atgatatgtg cattcccctt                    39

<210> SEQ ID NO 7
<211> LENGTH: 39
<212> TYPE: DNA
<213> ORGANISM: Homo sapiens

<400> SEQUENCE: 7
aaaaggatcc ctatgtcttc agacagtctt gctaaattt                     39

<210> SEQ ID NO 8
<211> LENGTH: 39
<212> TYPE: DNA
<213> ORGANISM: Homo sapiens

<400> SEQUENCE: 8
aaaactcgag aattaaatgg atcgaatatg tatattcac                     39

<210> SEQ ID NO 9
<211> LENGTH: 36
<212> TYPE: DNA
<213> ORGANISM: Homo sapiens

<400> SEQUENCE: 9
aaaactcgag ctatgacaac tcaagcaccg acgttt                        36

<210> SEQ ID NO 10
<211> LENGTH: 36
<212> TYPE: DNA
<213> ORGANISM: Homo sapiens

<400> SEQUENCE: 10
aaaaggatcc aactgtgatg atatgtgcat tccctt                        36

<210> SEQ ID NO 11
<211> LENGTH: 39
<212> TYPE: DNA
<213> ORGANISM: Homo sapiens

<400> SEQUENCE: 11
aaaactcgag ctatgtcttc agacagtgtt gctaaattt                     39

<210> SEQ ID NO 12
<211> LENGTH: 39
<212> TYPE: DNA
<213> ORGANISM: Homo sapiens

<400> SEQUENCE: 12
aaaaggatcc aaaatggatc gaatatgtat attcacagt                     39

<210> SEQ ID NO 13
<211> LENGTH: 22
<212> TYPE: PRT
<213> ORGANISM: Homo sapiens

<400> SEQUENCE: 13

Leu Ser Ala Glu Glu Glu Gly Leu His Ser Ala Glu Leu Gln Leu Ser
1               5                   10                  15
```

Lys Ile Asn Glu Thr Leu
            20

<210> SEQ ID NO 14
<211> LENGTH: 22
<212> TYPE: PRT
<213> ORGANISM: Homo sapiens

<400> SEQUENCE: 14

Leu Pro Glu Glu Glu Glu Val Leu Pro Glu Glu Glu Glu Val Leu Pro
1               5                   10                  15

Glu Glu Glu Glu Val Leu
            20

<210> SEQ ID NO 15
<211> LENGTH: 22
<212> TYPE: PRT
<213> ORGANISM: Homo sapiens

<400> SEQUENCE: 15

Leu Leu Arg Arg Arg Arg Ser Leu Ser Pro Thr Tyr Ile Glu Leu Met
1               5                   10                  15

Arg Pro Val Ser Glu Leu
            20

<210> SEQ ID NO 16
<211> LENGTH: 10
<212> TYPE: PRT
<213> ORGANISM: Homo sapiens

<400> SEQUENCE: 16

Phe Lys Lys Lys Leu Thr Ser Leu Arg Leu
1               5                   10

<210> SEQ ID NO 17
<211> LENGTH: 7
<212> TYPE: PRT
<213> ORGANISM: Homo sapiens

<400> SEQUENCE: 17

Met Ala Leu Met Leu Ile Val
1               5

<210> SEQ ID NO 18
<211> LENGTH: 11
<212> TYPE: PRT
<213> ORGANISM: Homo sapiens

<400> SEQUENCE: 18

Ile Lys Lys Asp Asp Leu Arg Glu Leu Gly Leu
1               5                   10

<210> SEQ ID NO 19
<211> LENGTH: 10
<212> TYPE: PRT
<213> ORGANISM: Homo sapiens

<400> SEQUENCE: 19

Leu Asp Ile Leu Lys Thr Asp Leu Ser Leu
1               5                   10

<210> SEQ ID NO 20
<211> LENGTH: 10
<212> TYPE: PRT

<213> ORGANISM: Homo sapiens

<400> SEQUENCE: 20

Leu Thr Thr Lys Glu Ile Lys Leu Glu Leu
1               5                   10

<210> SEQ ID NO 21
<211> LENGTH: 9
<212> TYPE: PRT
<213> ORGANISM: Homo sapiens

<400> SEQUENCE: 21

Leu Arg Leu Glu Glu Glu Leu Glu Leu
1               5

<210> SEQ ID NO 22
<211> LENGTH: 7
<212> TYPE: PRT
<213> ORGANISM: Homo sapiens

<400> SEQUENCE: 22

Pro Lys Lys Lys Arg Lys Val
1               5

<210> SEQ ID NO 23
<211> LENGTH: 16
<212> TYPE: PRT
<213> ORGANISM: Homo sapiens
<220> FEATURE:
<221> NAME/KEY: misc_feature
<222> LOCATION: (3)..(12)
<223> OTHER INFORMATION: Xaa can be any naturally occurring amino acid

<400> SEQUENCE: 23

Lys Arg Xaa Xaa Xaa Xaa Xaa Xaa Xaa Xaa Xaa Xaa Lys Lys Lys Leu
1               5                   10                  15

<210> SEQ ID NO 24
<211> LENGTH: 9
<212> TYPE: PRT
<213> ORGANISM: Homo sapiens

<400> SEQUENCE: 24

Leu Pro Pro Leu Glu Arg Leu Thr Leu
1               5

<210> SEQ ID NO 25
<211> LENGTH: 5
<212> TYPE: PRT
<213> ORGANISM: Homo sapiens

<400> SEQUENCE: 25

Lys Lys Thr Lys Thr
1               5

<210> SEQ ID NO 26
<211> LENGTH: 36
<212> TYPE: DNA
<213> ORGANISM: Homo sapiens

<400> SEQUENCE: 26
aaaaggatcc aacttcatta ttgcttcttg agttac                                 36

<210> SEQ ID NO 27
<211> LENGTH: 36
<212> TYPE: DNA

<213> ORGANISM: Homo sapiens

<400> SEQUENCE: 27
aaaaggatcc aaagtaattt cttcagaaat tctagt                36

<210> SEQ ID NO 28
<211> LENGTH: 36
<212> TYPE: DNA
<213> ORGANISM: Homo sapiens

<400> SEQUENCE: 28
aaaaggatcc aatcgggttt gtcttgattc tgagat                36

<210> SEQ ID NO 29
<211> LENGTH: 36
<212> TYPE: DNA
<213> ORGANISM: Homo sapiens

<400> SEQUENCE: 29
aaaaggatcc aaattggtgg catttactga ataggt                36

<210> SEQ ID NO 30
<211> LENGTH: 33
<212> TYPE: DNA
<213> ORGANISM: Homo sapiens

<400> SEQUENCE: 30
aaaactcgag cttcgactgc tcagatctca gaa                33

<210> SEQ ID NO 31
<211> LENGTH: 33
<212> TYPE: DNA
<213> ORGANISM: Homo sapiens

<400> SEQUENCE: 31
aaaactcgag ctggccgcgc taaactgacg atc                33

<210> SEQ ID NO 32
<211> LENGTH: 36
<212> TYPE: DNA
<213> ORGANISM: Homo sapiens

<400> SEQUENCE: 32
aaaactcgag ctgtgagact ccaagtgaga gtgact                36

<210> SEQ ID NO 33
<211> LENGTH: 36
<212> TYPE: DNA
<213> ORGANISM: Homo sapiens

<400> SEQUENCE: 33
aaaactcgag ctagcgttgg aagagctact tcgact                36

<210> SEQ ID NO 34
<211> LENGTH: 24
<212> TYPE: DNA
<213> ORGANISM: Homo sapiens

<400> SEQUENCE: 34
tccgctagcg ctaccggtcg ccac                24

<210> SEQ ID NO 35
<211> LENGTH: 83
<212> TYPE: DNA

```
<213> ORGANISM: Homo sapiens

<400> SEQUENCE: 35
aaaaagcttt taaacaattg tctttgtctt tttagcaggt acttcttctt caccttgaac    60
cttgtacagc tcgtccatgc cga                                           83

<210> SEQ ID NO 36
<211> LENGTH: 65
<212> TYPE: DNA
<213> ORGANISM: Homo sapiens

<400> SEQUENCE: 36
aaaaagcttt taaacaattg tctttgtctt tttagcaggt accttgtaca gctcgtccat    60
gccga                                                               65

<210> SEQ ID NO 37
<211> LENGTH: 56
<212> TYPE: DNA
<213> ORGANISM: Homo sapiens

<400> SEQUENCE: 37
aaaaagcttt tatgtctttg tcttttttagc agggctgtac agctcgtcca tgccga       56

<210> SEQ ID NO 38
<211> LENGTH: 50
<212> TYPE: DNA
<213> ORGANISM: Homo sapiens

<400> SEQUENCE: 38
aaaaagcttt tatgtctttg tctttttgct gtacagctcg tccatgccga               50
```

NUCLEAR TARGETING SEQUENCE

The present application claims priority to U.S. Provisional Application No. 60/633,243, filed Dec. 3, 2004, which is incorporated herein by reference.

The Sequence Listing associated with this application is filed in electronic format via EFS-Web and is hereby incorporated by reference into the specification in its entirety. The name of the text file containing the Sequence Listing is 4647_091 072_ST25.txt. The size of the text file is 6,932 Bytes, and the text file was created on Aug. 8, 2012.

BACKGROUND OF THE INVENTION

1. Field of the Invention

The present invention relates generally to the translocation of proteins and other compounds into and out of the nucleus of cells and, more particularly, relates to novel nuclear localization signal sequences and nuclear export signal sequences and their uses, such as, for example and without limitation, regulation of nucleic acid expression, transfection of eukaryotic cells, gene therapy, protection from toxic chemicals, transport of anti-cancer agents, etc.

2. Description of Related Art

The exchange of macromolecules between the cytoplasm and the cell nucleus is a basic biological process in eukaryotic cells central to the regulation of gene expression (which underlies all aspects of development, morphogenesis, and signaling pathways in eukaryotic organisms). Nuclear traffic occurs exclusively through the nuclear pore complex (NPC), a huge multi-proteic complex which lies across the nuclear membrane. While small molecules (up to 40-60 kDa) can diffuse through the NPC, nuclear import of larger molecules, such as proteins, is mediated by specific nuclear localization signal (NLS) sequences contained either in the transported molecule (Garcia-Bustos et al., Biochim. Biophys. Acta 1071:83-101, 1991) or contained in a shuttle protein which binds to the protein being transported.

NLS sequences typically are small, mostly basic, amino acid sequences which can be classified into three general groups: (i) a monopartite NLS exemplified by the SV40 large T antigen NLS (PKKKRKV) (SEQ ID NO: 22) (ii) a bipartite motif consisting of two basic domains separated by a variable number of spacer amino acids and exemplified by the Xenopus nucleoplasmin NLS (KR)OCXXXXXXXXKKKL) (SEQ. ID NO: 23) and (iii) noncanonical sequences such as M9 of the hnRNP A1 protein, the influenza virus nucleoprotein NLS, and the yeast Gal4 protein NLS (Dingwall and Laskey, Trends Biochem Sci 16:478-481, 1991).

The steps involved in the import mechanism of proteins into eukaryotic nuclei have been elucidated (Nigg, E. A., Nature, 386:779-87, 1997; Gorlich, D., EMBO J., 17:2721-7, 1998). To be transported, the NLS sequence is recognized by members of the importin family of proteins (also referred to as karyopherins), which then act as carriers to transport the substrate protein across the NPC. Inside the nucleus, the importin-substrate complex dissociates, liberating the substrate protein, and the importin carrier ultimately returns to the cytoplasm. The small GTPase Ran plays a pivotal role in this process by promoting, in its GTP-bound form, the dissociation of the import complex and the subsequent recycling of the importin carrier.

Once in the nucleus, many proteins are transported back to the cytoplasm as an essential step in their biological function. The export of macromolecules from the nucleus also relies on the existence of a specific signal in the substrate to be exported. For example, the Rev protein of human immunodeficiency virus type 1 (HIV-1) exits the nucleus, facilitating export of the unspliced viral RNA (Pollard and Malim, Ann. Rev. Microbiol., 52:491-532, 1998). Rev protein nuclear export is mediated by a specific nuclear export signal (NES) sequence consisting of the leucine-rich sequence, LPPLER-LTL (SEQ ID NO: 24), found also in proteins of other viruses (Dobbeistein et al., EMBO J. 16:4276-4284, 1997). Additionally, numerous cellular proteins, such as I-KB and MAPKK, contain potential NES sequences that may regulate the biological activity of these proteins by controlling their nuclear export (Ulinian et al., Cell 90:967-970, 1997). Known NES sequences essentially are short, leucine-rich, hydrophobic peptide motifs which mediate the handling of the substrate by other members of the importin β family of proteins, called exportins. Nuclear import and export processes thus are tightly linked.

The relatively small size of the NLS and NES sequences and, more importantly, the lack of clear and consistent consensus motifs in these signals, make it difficult to predict their presence in a given protein based solely on the analysis of its amino acid sequence. Furthermore, even if a consensus NLS or NES is found, it may not represent a functional signal. For example, β-glucuronidase (GUS), a commonly-used reporter enzyme which resides exclusively in the cell cytoplasm, carries a perfect, albeit non-functional, bipartite NLS sequence at its carboxy terminus. The only practical way to identify active NLS or NES sequences is by microinjecting (Guralnick et al., Plant Cell 8:363-373, 1996) or expressing the protein of interest in eukaryotic cells (Varagona et al., Plant Cell 3:105-113, 1991), heterokaryon formation (Michael et al., Cell 83:415-422, 1995), or using an in vitro transport system (Ossareh-Nazari et al., Science, 278:141-144, 1997).

A need exists, therefore, for determining new and unique NLS sequences which can translocate proteins and other compounds effectively and efficiently into or out of the cell nucleus.

SUMMARY OF THE INVENTION

The present invention fulfills this need by providing nuclear localization signaling (NLS) sequences derived from titin, a large muscle protein, comprised of amino acids 181-220: SVGRATSTAE LLVQGEEEVP AKKTKTIVST AQIS-ESRQTR (SEQ ID NO: 1) and fragments thereof.

Fragments of the NLS sequences derived from titin include, without limitation, amino acids 193-208: VQGEEEVP AKKTKTIV (SEQ ID NO: 2); amino acids 199-208: VPAKKTKTIV (SEQ ID NO: 3); or amino acids 200-206: PAKKTKT (SEQ ID NO: 4).

The NLS sequences can be linked to one or more agents, such as peptides, proteins or nucleotides, in order to transport the agents into the nucleus of mammalian, preferably human, cells.

In an embodiment of the present invention, the NLS sequences linked to one or more agents also can be linked to binding reagents, such as antibodies or ligands, to form an NLS-agent-antibody or NLS-agent-ligand complex, which is capable of binding to specific cell surface-expressing antigens or receptors, respectively, on the plasma membranes of cells. The complexes then enter into the cytoplasm of the cells by endocytosis, after which they are transported into the nucleus of the cells through an importin-NLS pathway.

In another embodiment, a method is provided for constructing cDNAs comprising combining an NLS sequence of the present invention with a nucleic acid sequence for a target protein in order to provide a mechanism for expression and entry of the target protein into the nucleus of cells, which then can perform one or more specific functions, such as, without limitation, protecting the nucleus from toxic chemicals, radiation or other DNA-modifying agents; regulation of transcription, development or differentiation; induction of DNA arrest (blockade); apoptosis (cell death) or DNA synthesis; delivery of anti-cancer agents to rapidly dividing cells, or any procedure where an agent is to be localized to the nucleus of a target cell for any purpose.

In a further embodiment, kits are provided which contain an NLS sequence of the present invention combined with a cDNA or RNA construct to form an NLS-cDNA or NLS-RNA construct in order to transfect DNA or RNA of cells. The NLS-cDNA or NLS-RNA constructs are targeted to the nucleus of a cell where they are incorporated into the genome of the cell and then expressed as a mRNA, ultimately to be translated into one or more proteins. Other NLS-cDNA or NLS-RNA constructs can transfer silencing RNA into the nucleus of a cell in order to interfere with transcription of a native mRNA.

Figure 1:
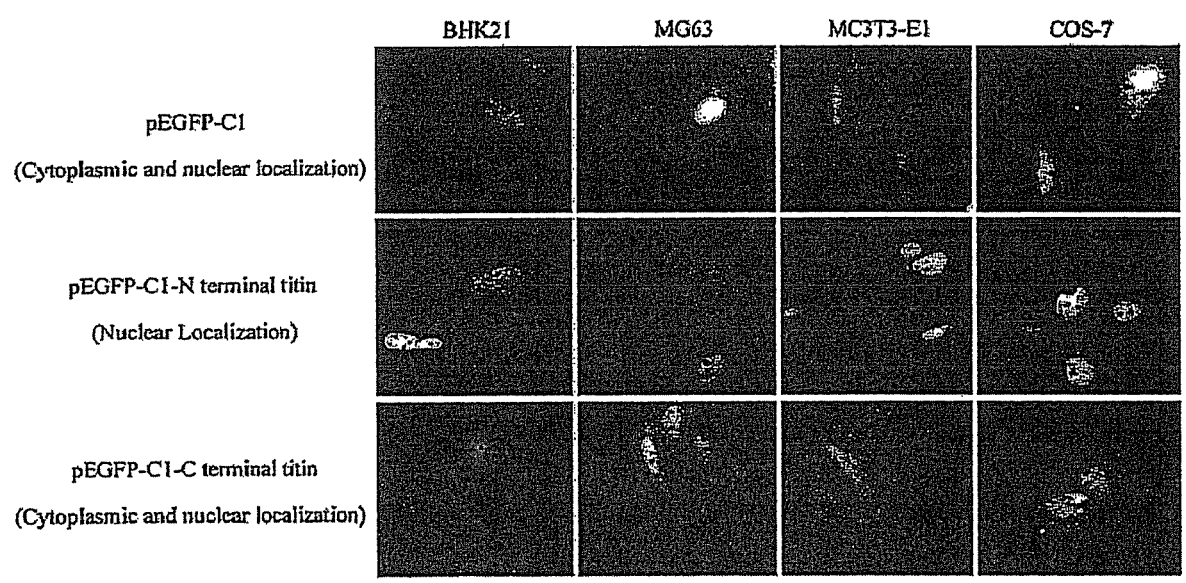
FIG. 1 illustrates the transient expression of pEGFP-C1 constructs in four different cell lines. Stars indicate nuclear localization and arrows indicate cytoplasmic localization.

Table 1 lists the primers used to make the NLS-localizing constructs in pEGFPC1 (NF-1 forward, SEQ ID NO: 9; NF-1 reverse, SEQ ID NO: 26; NF-2 forward, SEQ ID NO: 9; NF-2 reverse, SEQ ID NO: 27; NF-3 forward, SEQ ID NO: 9; NF-3 reverse, SEQ ID NO: 28; NF-4 forward, SEQ ID NO: 9; NF-4 reverse, SEQ ID NO: 29; NF-5 forward, SEQ II) NO: 30: NF-5 reverse, SEQ ID NO: 10; NF-6 forward, SEQ ID NO: 31; NF-6 reverse, SEQ ID NO: 28; NF-7 forward, SEQ ID NO: 32; NF-7 reverse, SEQ II) NO: 28; NF-8 forward, SEQ ID NO: 33; NF-8 reverse, SEQ ID NO: 28; NF-9 forward, SEQ 11) NO: 34; NF-9 reverse, SEQ ID NO: 35; NF-10 forward, SEQ ID NO: 34; NF-10 reverse, SEQ ID NO: 36; NF-11 forward, SEQ ID NO: 34: NF-11 reverse, SEQ ID NO: 37: NF-12 forward, SEQ ID NO: 34; NF-12 reverse, SEQ ID NO: 38).

Table 2 provides the predicted NES sequences in human titin (N-terminus, Novex I, Novex III, N2B, N2A, C-terminus, SEQ ID NOS: 16-21, respectively).

DESCRIPTION OF THE PREFERRED EMBODIMENTS

The present invention provides for the first time nuclear localization signaling (NLS) sequences derived from the large muscle protein, titin, comprised of amino acids 181-220: SVGRATSTAE LLVQGEEEVP AKKTKTIVST AQIS-ESRQTR (SEQ ID NO: 1) and fragments thereof. Fragments of the NLS sequences derived from the titin protein include, without limitation, amino acids 193-208: VQGEEEVP AKK-TKTIV (SEQ ID NO: 2); amino acids 199-208: VPAKKTK-TIV (SEQ ID NO: 3); or amino acids 200-206: PAKKTKT (SEQ ID NO: 4).

The NLS sequences can be linked to agents, such as peptides, proteins or nucleotides, in order to transport the agents into the nucleus of mammalian, preferably human, cells.

In an embodiment of the present invention, the NLS sequences linked to one or more agents also can be linked to binding reagents, such as antibodies or ligands, to form an NLS-agent-antibody or NLS-agent-ligand complex, which is capable of binding to specific cell surface-expressing antigens or receptors, respectively, on the plasma membranes of cells. The complexes then enter into the cytoplasm of the cells by endocytosis, after which they are transported into the nucleus of the cells through an importin-NLS pathway.

In another embodiment, a method is provided for constructing cDNAs, comprised of combining a NLS sequence of the present invention with a nucleic acid sequence for a target protein in order to provide a mechanism for expression and entry of the target protein into the nucleus of cells, which then can perform one or more specific functions, such as, without limitation, protecting the nucleus from toxic chemicals, radiation or other DNA-modifying agents; regulation of transcription, development or differentiation; induction of DNA arrest (blockade); apoptosis (cell death) or DNA synthesis; delivery of anti-cancer agents to rapidly dividing cells, or any procedure where an agent is to be localized to the nucleus of a target cell for any purpose.

In a further embodiment, kits are provided which contain an NLS sequence of the present invention combined with a cDNA or RNA construct to form an NLS-cDNA or NLS-RNA construct in order to transfect DNA or RNA of cells. The NLS-cDNA or NLS-RNA constructs can be targeted to the nucleus of a cell where they are incorporated into the genome of the cell and then expressed as a mRNA, ultimately to be translated into one or more proteins. Other NLS-cDNA or NLS-RNA constructs can transfer silencing RNA into the nucleus of a cell in order to interfere with transcription of a native mRNA.

As used herein, the terms "peptide," "polypeptide," and "protein" are used interchangeably and refer to any polymer of amino acids (dipeptide or greater) linked through peptide bonds. Thus, the terms "peptide," "polypeptide," and "protein" include oligopeptides, protein fragments, analogues, nuteins, fusion proteins and the like.

As used herein, the terms "transfect," "transfection" or "transfecting" is meant to indicate the act or method of introducing a molecule, such as a nucleic acid or other compositions of the present invention including, but not limited to, peptides and proteins.

Meanings of the term "gene expression" are known to those with skill in the art. "Gene expression" includes the production of a protein from RNA or DNA and production of an RNA from a DNA. A gene is said to be "expressed" when it is transcribed into RNA, but this meaning also includes translation into a peptide or protein. The term "gene expression" is often shortened to "expression," "expressed," or the like. Additional meanings of the term "gene expression" are known to those with skill in the art.

The term "binding reagent" and like terms refer to any compound, composition or molecule capable of specifically or substantially specifically (that is with limited cross-reactivity) binding another compound or molecule, which, in the case of immune-recognition, is an epitope. A "binding reagent type" is a binding reagent or population thereof having a single specificity. The binding reagents typically are antibodies, preferably monoclonal antibodies, or derivatives or analogs thereof, but also include, without limitation: Fv fragments; single chain Fv (scFv) fragments; Fab' fragments; F(ab')2 fragments; humanized antibodies and antibody fragments; camelized antibodies and antibody fragments; and multivalent versions of the foregoing. Multivalent binding reagents also may be used, as appropriate, including without limitation: monospecific or bispecific antibodies, such as disulfide stabilized Fv fragments, scFv tandems ((scFv)2 fragments), diabodies, tribodies or tetrabodies, which typically are covalently linked or otherwise stabilized (i.e., leucine zipper or helix stabilized) scFv fragments. "Binding reagents" also can include aptamers, as are described in the art, as well as ligands that bind specific receptor moieties found on plasma membranes of cells.

Methods of making antigen-specific binding reagents, including antibodies and their derivatives and analogs and aptamers, are well-known in the art. Polyclonal antibodies to specific plasma membrane antigens can be generated by immunization of an animal. Monoclonal antibodies can be prepared according to standard (hybridoma) methodology. Antibody derivatives and analogs, including humanized antibodies can be prepared recombinantly by isolating a DNA fragment from DNA encoding a monoclonal antibody and subcloning the appropriate V regions into an appropriate expression vector according to standard methods. Phage display and aptamer technology is described in the literature and permit in vitro clonal amplification of antigen-specific binding reagents with very affinity low cross-reactivity. Phage display reagents and systems are available commercially, and include the Recombinant Phage Antibody System (RPAS), commercially available from Amersham Pharmacia Biotech, Inc. of Piscataway, N.J., and the pSKAN Phagemid Display System, commercially available from MoBiTec, LLC of Marco Island, Fla. Aptamer technology is described, for example and without limitation, in U.S. Pat. Nos. 5,270,163, 5,475096, 5,840867 and 6,544,776.

The NLS-nucleic acid-antibody or ligand constructs of the present invention can be formulated using a variety of non-covalent and covalent approaches to associate the NLS sequences to the nucleic acids, which then are associated with an antibody or ligand specific for an antigen or receptor, respectively, of a particular cell plasma membrane. A suitable protocol for the NLS-nucleic acid-antibody or ligand constructs of the present invention includes, for example, mixing the NLS sequence with a nucleic acid, such as cDNA or RNA, to form ionic complexes between the negatively charged DNA, the NLS sequence and the antibody or ligand. These complexes then can be used to transfect cells using conventional methods well known by those skilled in the art. Significant enhancement of transgene expression can be achieved following direct microinjection of the preformed NLS-nucleic acid-antibody or ligand constructs of the present invention into the cytoplasm of cells. Another suitable protocol for formulating the NLS-nucleic acid-antibody or ligand constructs of the present invention includes, for example, fusing or covalently binding the NLS sequence to a cationic moiety such as poly/oligolysine or a histone 1-DNA-binding domain, which then is covalently bonded to the antibody or ligand. Still another protocol for formulating the NLS-nucleic acid-antibody or ligand constructs of the present invention includes, for example, coupling the NLS sequences to a nucleic acid, such as cDNA or RNA, by chemically conjugating the NLS sequence to the nucleic acid, which then is chemically conjugated to the antibody or ligand. Crosslinking agents can include, for example and without limitation, cyclo-propapyrroloindole and 4-(N-maleimidomethyl)cyclohexane-1-carboxylic acid N-hydroxysuccinimide ester, together with photoactive p-azido-tetrafluoro-benzyl-NLS sequence conjugates. A further protocol for synthesizing the NLS-nucleic acid-antibody or ligand constructs of the present invention includes, for example, coupling streptavidin-conjugated NLS sequences to biotinylated nucleic acids, such as cDNA or RNA and biotinylated antibodies or ligands.

Any nucleic acid can be used in combination with the present invention. A useful nucleic acid encompasses any naturally occurring or synthetic nucleic acid, polynucleotide, derivative, or analogue thereof. One with ordinary skill in the art will be able to determine which nucleic acid is useful and will be able to construct the useful nucleic acid. Sequence information for many useful nucleic acids is available in databases known to one with skill in the art (see for example, McKusick, Mendelian Inheritance in Man. Catalogs of Human Genes and Genetic Disorders. Baltimore: Johns Hopkins University Press (1998, 12th ed.); and Online Mendelian Inheritance in Man, OMIM Center for Medical Genetics, Johns Hopkins University (Baltimore, Md.) and National Center for Biotechnology Information, National Library of Medicine (Bethesda, Md.) (1999) World Wide Web URL: "http://www.ncbi.nlm.nih.gov/omim"). Alternatively, many useful nucleic acids are commercially available. In addition, one with ordinary skill in the art is able to determine the sequence of a region of nucleic acid using methods known in the art.

The nucleic acid can be, but is not limited to, single-stranded nucleic acid, double-stranded nucleic acid, polynucleotides, DNA, RNA, and single- or double-stranded viral nucleic acid. In certain preferred embodiments, the nucleic acid comprises an expression vector. The expression vector can include a gene sequence under the control of a promoter region which one with skill in the art can design to be compatible with a host cell, such that, the gene is expressed after transfer into the nucleus. In certain embodiments, the nucleic acid can be a plasmid, a circular nucleic acid, a linear nucleic acid, a viral vector, a therapeutic vector, and the like.

In certain embodiments, the nucleic acid comprises an antisense nucleic acid targeted to complementary sequences in the nucleus. Specifically, the bridging of introns, exons, and intron-exon boundaries is contemplated with antisense strands or antisense encoding vectors. In certain embodiments, the nucleic acid encodes an expression product, wherein the expression product comprises a peptide, a polypeptide, a protein, a fusion protein, or an antisense nucleic acid. In certain embodiments, the NLS-cDNA or NLS-RNA has an antisense activity, wherein the antisense activity is localized in the nucleus, not in the cytoplasm, because the NLS directs the complex to the nucleus and retains it in the nucleus. In certain embodiments wherein an antisense nucleic acid is expressed from a nucleic acid annealed to an NLS-cDNA or NLS-RNA, the antisense reaction can take place in any compartment of a cell or even outside of a cell. In certain embodiments, the nucleic acid encodes a gene, a reporter gene, a gene fusion, a transgene, or a therapeutic gene.

In certain embodiments, the nucleic acid is a therapeutic vector (including plasmid, expression, viral, and the like) capable of expressing a therapeutic gene in the host cell (the cell into which the therapeutic vector is transferred). It is preferred that the therapeutic vector express the therapeutic gene product either constitutively or inducibly in the host cell. The NLS-cDNA or NLS-RNA can be annealed to the non-coding strand of a promoter having control over the expression of the gene product, wherein such design stimulates expression. The therapeutic vector can comprise a DNA vaccine.

Many desirable vectors, plasmids, expression vectors, DNAs, RNAs, oligonucleotides, strands of nucleic acid, and the like are readily available through commercial sources and are useful in certain embodiments of the present invention as a nucleic acid (e.g., Roche, Stratagene, In Vitrogene, Promega, PerSeptive Biosystems, Research Genetics, and the like). Additionally, a nucleic acid can be produced by techniques of molecular biology known to those of ordinary skill in the art (see e.g., Sambrook et al., Molecular Cloning: A Laboratory Manual, Second Edition (1989) Cold Spring Harbor Laboratory Press). The meaning of terms such as "expression vector," "vector," "expression construct," or "construct" that are used in certain embodiments are known to those of ordinary skill in the art. The terms "expression vector," "vector," "expression construct," or "construct" are used interchangeably and, in general, refer to any nucleic acid that encodes an expression product. The terms "expression vector," "vector," "expression construct," or "construct" also are known to one with skill in the art. In certain embodiments, the nucleic acid is expressed. In certain preferred embodiments, the resulting transcript may be translated into a protein, but it need not be. Thus, in certain embodiments, expression includes both transcription of a gene and translation of an RNA into a gene product.

Particularly useful vectors are contemplated to be those vectors in which a coding portion of the DNA segment, whether encoding a full length protein, polypeptide or smaller peptide, is positioned under the transcriptional control of a promoter. In certain aspects "promoter" refers to a DNA sequence recognized by the synthetic machinery of the cell, or introduced synthetic machinery, required to initiate the specific transcription of a gene.

The promoter may be in the form of the promoter that is naturally associated with a gene, as may be obtained by isolating the 5' non-coding sequences located upstream of the coding segment or exon, for example, using recombinant cloning and/or PCR™ technology In certain embodiments, the particular promoter that is employed to control the expression of a nucleic acid is not believed to be critical, so long as it is capable of expressing the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter. The selection and use of such particular promoters will be apparent to those with skill in the art (see, e.g., U.S. Pat. No. 5,858,774 to Malbon et al., incorporated herein by reference; Gene-Expression Systems (1998) Fernandez et al., eds. Academic Press; M. Kriegler, Gene Transfer and Expression: A Laboratory Manual (1991) Oxford University Press; and Gene Expression: General and Cell Type Specific (1993) M. Karin (ed.) Birkhauser).

The ability to specifically inhibit gene function in a variety of organisms utilizing antisense RNA or dsRNA-mediated interference (RNAi or dsRNA) is well-known in the field of molecular biology (see for example C. P. Hunter, 1999, Current Biology, 9:R440-442; Hamilton et al., 1999, Science, 286:950-952; and S. W. Ding, 2000, Current Opinions in Biotechnology, 11: 152-156, hereby incorporated by reference in their entireties). Interfering RNA, either double-stranded interfering RNA (dsRNAi or dsRNA) or RNA-mediated interference (RNAi), typically comprises a polynucleotide sequence identical or homologous to a target gene, or fragment of a gene, linked directly, or indirectly, to a polynucleotide sequence complementary to the sequence of the target gene or fragment thereof. The dsRNAi may comprise a polynucleotide linker sequence of sufficient length to allow for the two polynucleotide sequences to fold over and hybridize to each other, although a linker sequence is not necessary. The linker sequence is designed to separate the antisense and sense strands of RNAi significantly enough to limit the effects of steric hindrance and allow for the formation of dsRNAi molecules and should not hybridize with sequences within the hybridizing portions of the dsRNAi molecule. The specificity of this gene silencing mechanism appears to be extremely high, blocking expression only of targeted genes, while leaving other genes unaffected.

Accordingly, one method for disrupting a targeted gene according to the present invention includes associating a NLS sequence either to a dsRNA or RNAi, wherein the dsRNA or RNAi is comprised of polynucleotide sequences identical or homologous to the targeted gene or a homologue thereof. The terms "dsRNAi," "RNAi," and "siRNA" are used interchangeably herein unless otherwise noted.

RNA containing a nucleotide sequence identical to a fragment of the target gene is preferred for disruption; however, RNA sequences with insertions, deletions, and point mutations relative to the target sequence also can be used for inhibition. Sequence identity may be optimized by sequence comparison and alignment algorithms known in the art (see Gribskov and Devereux, *Sequence Analysis Primer*, Stockton Press, 1991, and references cited therein) and then calculating the percent difference between the nucleotide sequences by, for example, the Smith-Waterman algorithm as implemented in the BESTFIT software program using default parameters (e.g., University of Wisconsin Genetic Computing Group). Alternatively, the duplex region of the RNA may be defined functionally as a nucleotide sequence that is capable of hybridizing with a fragment of the target gene transcript.

RNA may be synthesized either in vivo or in vitro. Endogenous RNA polymerase of the cell may mediate transcription in vivo, or cloned RNA polymerase can be used for transcription in vivo or in vitro. For transcription from a transgene in vivo or an expression construct, a regulatory region (e.g., promoter, enhancer, silencer, splice donor and acceptor, polyadenylation) may be used to transcribe the RNA strand(s); the promoters may be known inducible promoters, such as baculovirus. The RNA strands may or may not be polyadenylated; the RNA strands may or may not be capable of being translated into a polypeptide by a cell's translational apparatus. RNA may be chemically or enzymatically synthesized by manual or automated reactions. The RNA may be synthesized by a cellular RNA polymerase or a bacteriophage RNA polymerase (e.g., T3, T7, SP6). The use and production of an expression construct are known in the art (see for example, WO 97/32016; U.S. Pat. Nos. 5,593,874; 5,698,425; 5,712,135; 5,789,214; and 5,804,693; and the references cited therein). If synthesized chemically or by in vitro enzymatic synthesis, the RNA may be purified prior to introduction into the cell. For example, RNA can be purified from a mixture by extraction with a solvent or resin, precipitation, electrophoresis, chromatography, or a combination thereof. Alternatively, the RNA may be used with no, or a minimum of, purification to avoid losses due to sample processing. The RNA may be dried for storage or dissolved in an aqueous solution. The solution may contain buffers or salts to promote annealing, and/or stabilization of the duplex strands.

Preferably, and most conveniently, dsRNAi can be targeted to an entire polynucleotide sequence of the targeted gene.

The present invention is more particularly described in the following non-limiting example, which is intended to be illustrative only, as numerous modifications and variations therein will be apparent to those skilled in the art.

EXAMPLE

Introduction

Titin is a giant protein expressed in cardiac, skeletal and smooth muscle tissues which is responsible for muscle elasticity and for providing a scaffold for assembly of sarcomeric proteins. The full length sequence of the titin gene contains 363 exons which encode a 4,200 kDa protein having 38,138 amino acid residues. The titin protein mainly is composed of immunoglobulin (Ig), fibronectin III (Fn-III) domains and PEVK repeats (a ~28 residue, P, E, V, K-enriched motif), which contribute to the elasticity of the titin protein. Different combinations of these domains determine the stiffness of titin and thus the stiffness of muscle tissue. Additional sarcomeric protein binding sites have been found on titin, confirming the key role that titin plays in the assembly of sarcomere units (Gautel M. et al., J. Cell Science, 109:2747-2754, 1996).

Monoclonal antibodies specific to titin have shown that single titin molecules extend across the entire distance from the Z-disk to the M-line and consequently span in vivo a distance of more than one micrometer. In its I-band section, the titin filament behaves elastically during muscle contraction, and thus is believed to account for most of the resting tension of striated muscle.

In addition to elastic elements contained in titin, there also are several titin-specific sequences and one kinase domain, although the exact role of these titin-specific sequences with respect to titin-related functions are not well understood.

Titin also is expressed in non-muscle tissues and cells (Banes, A. et al., Osteoarthritis and Cartilage, 7:141-153, 1999), and several isoforms of titin with quite different sizes have been reported (Wang, K. et al., Proc. Natl. Acad. Sci., USA, 88:7101-5, 1991), suggesting that titin may not be muscle-specific but rather may work as a universal elastic protein in tissues and organelles.

Analysis of the complete sequence of titin reveals that there are several titin-specific sequence insertions at its amino and carboxyl termini, with the exception of the Ig and FN III domains. Using the PSORT II program of Nakai and Horton (Trends Biochem. Sci., 24:34-36, 1999), a seven amino acid (amino acids 200-206) NLS sequence, PAKKTKT (SEQ ID NO: 4) was predicted. With the use of an enhanced green fluorescence protein (EGFP) reporter system, immunostaining and confocal microscopy techniques, the motif of 200-PAKKTKT-206 (SEQ ID NO: 4) was shown to be a functional NLS which directed the N-terminus of titin and EGFP into the nucleus in different cell lines, including human osteoblast-like MG63, BHK21, MC3T3-E1 and COS-7 cells, therefore showing for the first time that there is a functional NLS in human titin protein and substantiating evidence that titin may be transported into the nucleus of cells.

Experimental Procedures

Antibodies

Anti-titin antibodies (Z1Z2 recognizes the N-terminus of titin, M8M9 recognizes the C-terminus of titin) were received from the University of Mannheim, Germany. ALEX-AFLUOR® 568 conjugated goat anti-rabbit IgG (H+L) was obtained from Molecular Probes (Eugene, Oreg.).

Primers

All primers used in the study were synthesized by MWG Biotech, Inc. (High Point, N.C.).

Prediction of Nuclear Localization Signal (NLS) Sequences

The potential NLS sequences in the N- and C-termini of human titin protein were predicted using three web-based programs: NucPred, PredictNLS and the PSORT II program (Cokol, M. et al., EMBO Rep., 1:411-415, 2000; Nair, R. et al., Proteins, 53:917-930, 2003; Nakai, K. et al., Trends Biochem. Sci., 24:34-36, 1999).

Molecular Cloning

The N-terminal and C-terminal fragments of human titin were amplified and cloned into pcDNA3.1 (Invitrogen, Carlsbad, Calif.) and pEGFP (BD Biosciences Clontech, Mountain View, Calif.) vectors, respectively. The N-terminus was comprised of residues 1-790, including domains Z1, Z2 and Z repeats. The C-terminus was comprised of residues 33,791-34,350, including domains M7-10.

For pcDNA3.1 constructs, the N- and C-terminal fragments of the human sequence were amplified using primers: N-terminus, 5'-AAA AGG ATC CCT ATG ACA ACT CAA GCA CCG ACG TTT-3' (forward) (SEQ ID NO: 5) and 5'-AAA ACT CGA GAA TTA CTG TGA TGA TAT GTG CAT TCC CTT-3' (reverse) (SEQ ID NO: 6); C-terminus, 5'-AAA AGG ATC CCT ATG TCT TCA GAC AGT GTT GCT AAA TTT-3' (forward) (SEQ ID NO: 7) and 5'-AAA ACT CGA GAA TTA AAT GGA TCG AAT ATG TAT ATT CAC-3' (reverse) (SEQ ID NO: 8). For pEGFP constructs, the primers were: N-terminus, 5'-AAAA ACT CGA GCT ATG ACA ACT CAA GCA CCG ACG TTT-3' (forward) (SEQ ID NO: 9) and 5'-AAA AGG ATC CAA CTG TGA TGA TAT GTG CAT TCC CTT-3' (reverse) (SEQ ID NO: 10); C-terminus, 5'-AAA ACT CGA GCT ATG TCT TCA GAC AGT GTT GCT AAA TTT-3' (forward) (SEQ ID NO: 11) and 5'-AAA AGG ATC CAA AAT GGA TCG AAT ATG TAT ATT CAC AGT-3' (reverse) (SEQ ID NO: 12).

In the constructs of the C-terminus, a start codon was added at the 5' end. In the pcDNA3.1 constructs, a stop codon (TAA) was added at the end of both N- and C-terminal fragments of titin due to the lack of stop codons in the pcDNA3.1 plasmid. The fragments of titin were amplified from human skeletal muscle total RNA (Ambion, Austin, Tex., #7982) and cloned into pcDNA3.1 at BamH I-Xho sites or pEGFP-C1 and N1 at Xho I-BamH I sites. NLS-localizing constructs, also referred to as nuclear fragments (NFs) 1-7 were cloned in pEGFP-C1 at Xho I-BamH I sites. NFs 8-10 were cloned in pEGFP-C1 at Nhe I-Hind III sites. The primers used for making these NF constructs are shown in Table 1. To reduce the effects of the C-terminal lysine residue of GFP on the nuclear localization of NFs 8-10, it was mutated to serine in these three constructs (shown in Table 1).

Transfection of Mammalian Cells

The constructs were transformed into the DH5α strain of *E. coli* (Invitrogen, Carlsbad, Calif.) and the transformed bacteria were selected on LB selective medium containing 50 µg/ml kanamycin (Sigma St. Louis, Mo.). The construct plasmids were purified from DH5α using the plasmid Maxi kit from QIAGEN (Valencia, Calif.). The pEGFP or pcDNA3.1 constructs were transfected into MC3T3-E1 cells (a mouse osteoblast-like cell line), BHK21 cells (derived from hamster kidney cells), COS-7 (derived from monkey kidney cells) or MG63 cells (obtained from a human osteosarcoma) using lipofectamine (Invitrogen, Carlsbad, Calif.) according to the manufacturer's protocol. The stable transfectants of MG63 were selected using G418 (Invitrogen, Carlsbad, Calif.) 48 hours post-transfection at 500 µg/ml. The cells were incubated with G418 for up to three weeks until individual colonies were formed. The colonies with green fluorescence were selected using an Olympus BH61 fluorescence microscope. The colonies expressing N- or C-terminal fragments of titin were selected by immunostaining. The stable transfectants of MG63 were kept in MEM medium (Invitrogen, Carlsbad, Calif.) containing 100 µg/ml G418.

Immunostaining of the N-Terminus and C-Terminus of Titin Expressed in COS-7 Cells N-terminal and C-terminal pcDNA3.1 titin constructs were transfected into COS-7 cells. The transiently transfected COS-7 cells were fixed with 3.7% formaldehyde at room temperature for 30 minutes and permeabilized with 0.1% Triton X-100 at room temperature for 15 minutes. After washing with phosphate-buffered saline (PBS, Invitrogen, Carlsbad, Calif.), the cells were blocked with 5% bovine serum albumin (BSA, Fisher Scientific, Suwanee, Ga.) and 2% goat serum (Sigma, St. Louis, Mo.) at 37° C. for 2 hours, then were labeled with anti-titin antibody ZIZ2 or M8M9 (1:10 diluted in PBS) at 37° C. for 2 hours, then washed with PBS two times, 5 minutes per wash. The proteins were visualized with ALEXAFLUOR® 568-conjugated goat, anti-rabbit IgG (1:500 diluted in PBS) at 37° C. for 1 hour. The stained cells were mounted on glass slides using a SLOWFADE® light antifade kit (Molecular Probes, Eugene, Oreg.) containing 100 ng/ml 4,6-diamidino-2-phenylindole (DAPI, Sigma, St. Louis, Mo.). The images of the cells were viewed using a regular fluorescence microscope (Olympus BX60, OPELCO, Dulles, Va.) or a LeicaSP2 AOBS laser scanning confocal microscope (Leica Microsystem, Inc., Exton, Pa.) with a 40× oil immersion objective.

Prediction of Nuclear Export Signals (NES) Sequences

The amino acid sequences of the domains containing titin-specific sequences were retrieved from Genbank and input to a web-based NES prediction program, Net NES 1.1 (La Cour et al., Protein Eng. Des. Sel., 17:527-536, 2004). The amino acid residue numbering was derived from the corresponding entries and was not the same for all the domains due to the use of different entries.

Results

Figure 2:
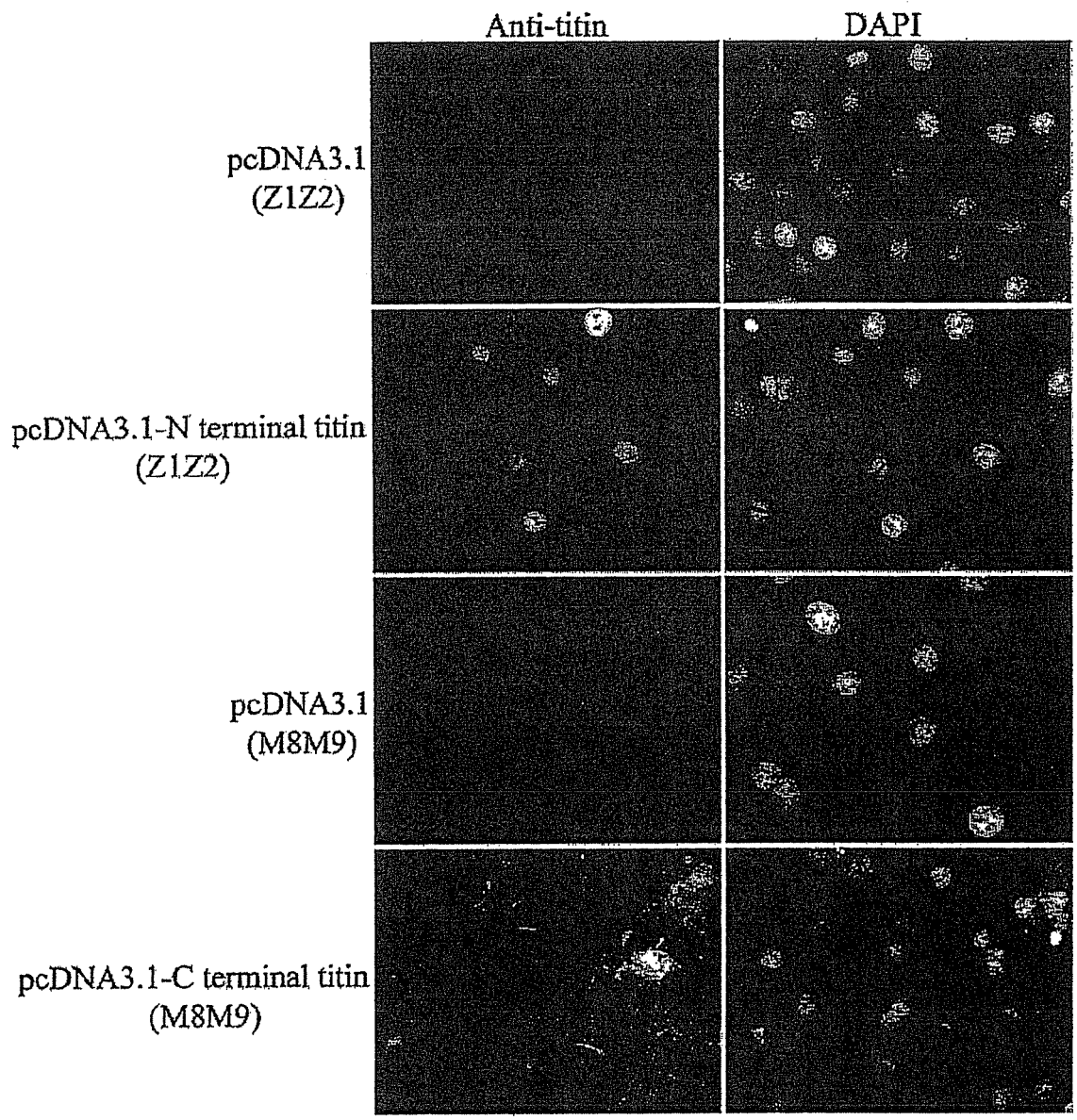
FIG. 2 illustrates intracellular localization of titin N- and C-terminus fragments in COS-7 cells.

Nuclear Localization of Titin N-Terminal Fragment-GFP Fusion Proteins in Mammalian Cells In all of the tested cell lines, the titin N-terminal fusion proteins localized principally in the nucleus in both high-expressing and low-expressing cells, while the titin C-terminal GFP fusion proteins and GFP only control proteins distributed in both the nucleus and the cytoplasm (FIG. 1). To confirm that the intracellular localization of the N- and C-terminal fragments of human titin protein was not due to the effects of GFP fusion, the tag-free fragments were also cloned into pcDNA3.1 and transfected into COS-7 cells. The transiently expressed titin fragments in COS-7 cells were stained with anti-titin antibodies. The results confirmed the finding of GFP fusion constructs. As shown in FIG. 2, the N-terminal fragment of titin mainly was in the nucleus while the C-terminal fragment of titin was mainly in the cytoplasm. As confirmed by DAPI staining, the titin N-terminal fragments clearly were in the nucleus and not in the nucleolus.

Figure 3:
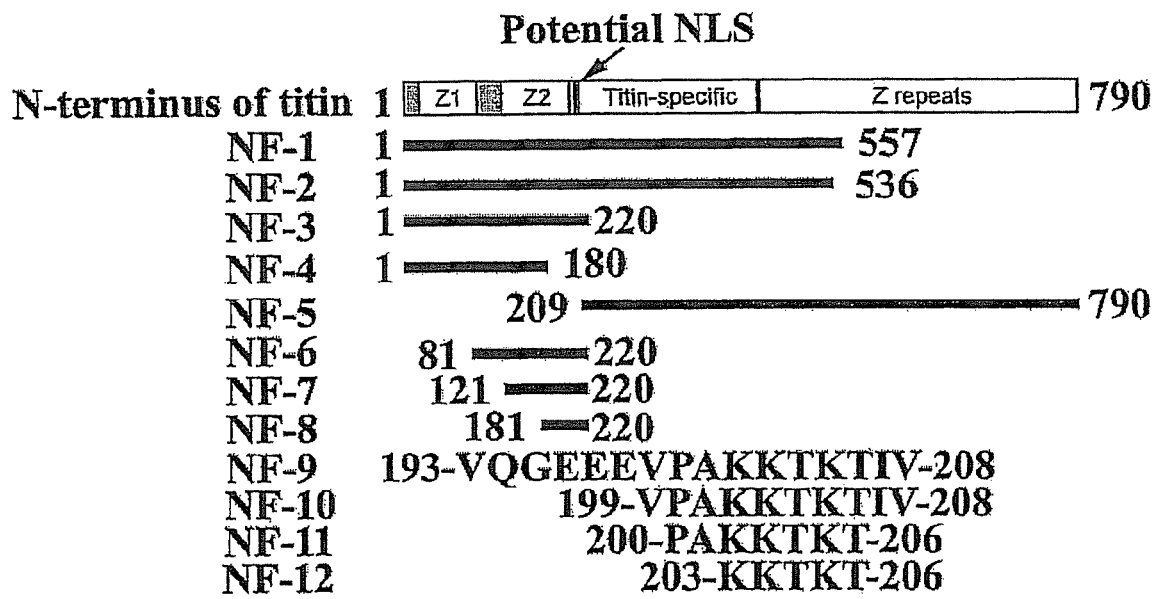
FIG. 3 is a design of subclones of human titin N-terminus for searching potential nuclear localization signal (NLS) sequences (NF-9. NF-10, NF-11 and NF-12, SEQ ID NOS: 2, 3, 4, and 25, respectively.

Prediction of Potential Nuclear Localization Signals in Amino and Carboxyl Termini of Human Titin The sequences of titin N- and C-termini were input to three web-based programs as described in the experimental protocol section. No NLS sequences were predicted within the C-terminus of human titin from any of the programs. Negative results on the N-terminus were obtained from programs PredictNLS and NucPred. One potential NLS sequence within the N-terminus of human titin was predicted by PSORT II: 200-PAKKTKT-206 (pat7) (SEQ ID NO: 4) (Nakai K. et al., Trends Biochem. Sci., 24:34-36, 1999). There were three types of NLS sequences based on the classification of the PSORT II program. Pat4 was composed of four basic amino acids (K or R), or composed of three basic amino acids (K or R) and either H or P. Pat7 was a pattern of NLS sequences starting with P and followed within 3 residues by a basic segment containing 3 of 4 K/R residues. It has been shown that bipartite NLS sequences are composed of 2 basic residues, a 10-residue spacer and another basic region consisting of at least 3 of 5 basic residues (Nakai K. et al., Trends Biochem. Sci., 24:34-36, 1999; Robbins, J. et al., Cell, 64:615-623, 1991). The predicted potential NLS sequence was located in the titin-specific sequence between the Z2 domain and Z repeats (FIG. 3).

By using the PSORT II program, three potential DNA-binding motifs were predicted: 3460-LSAEEEGLH-SAELQLSKINETL-3481 (SEQ ID NO: 13), 11047-LPEEEEVLPEEEEVLPEEEEVL-11068 (SEQ ID NO: 14), and 33195-LLRRRRSLSPTYIELMRPVSEL-33218 (SEQ ID NO: 15).

PAKKTKT is a Functional NES Sequence

Figure 4:
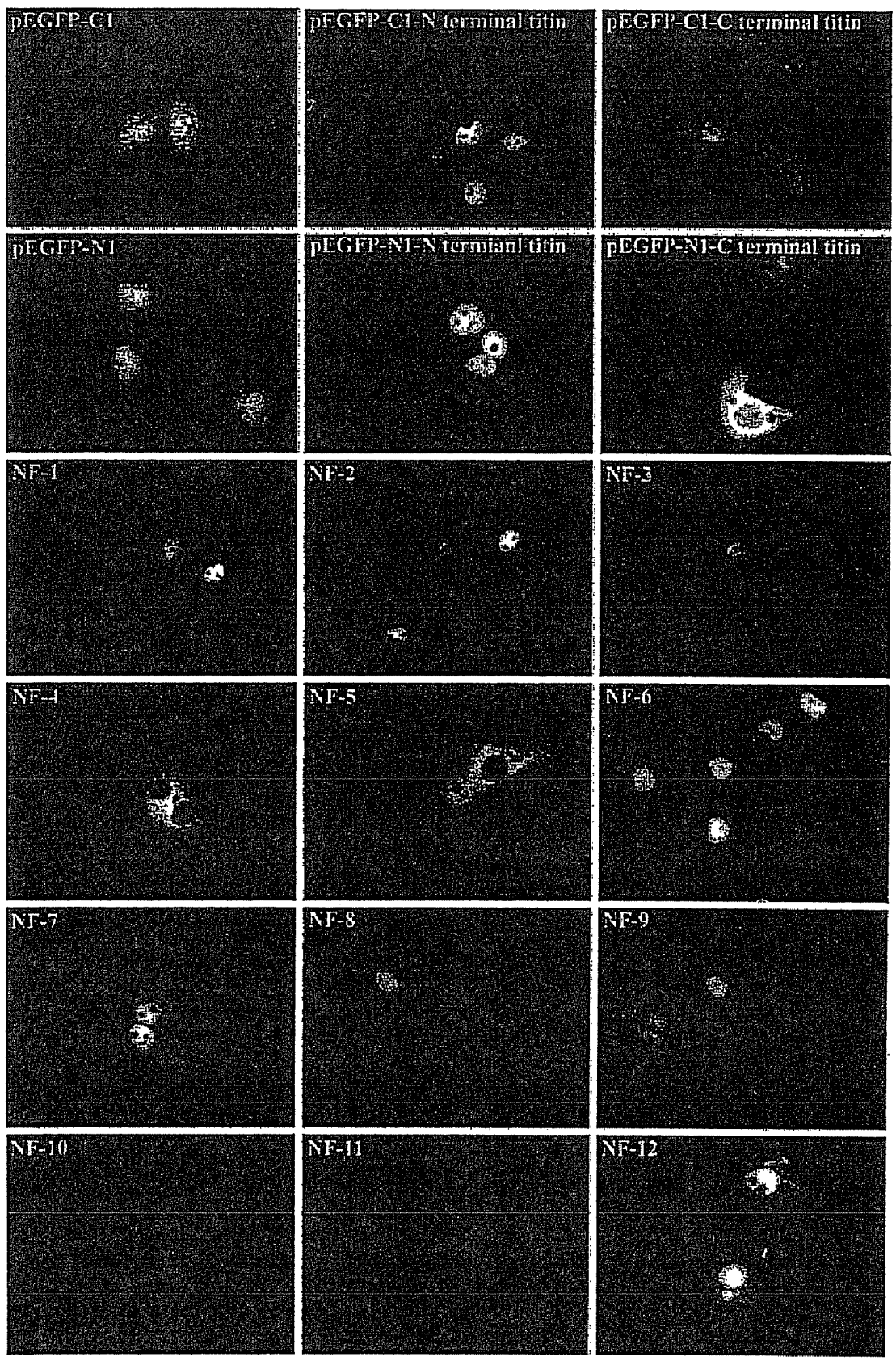
FIG. 4 illustrates the intracellular localization of subclones of human titin N-terminus in COS-7 cells.
Figure 5:
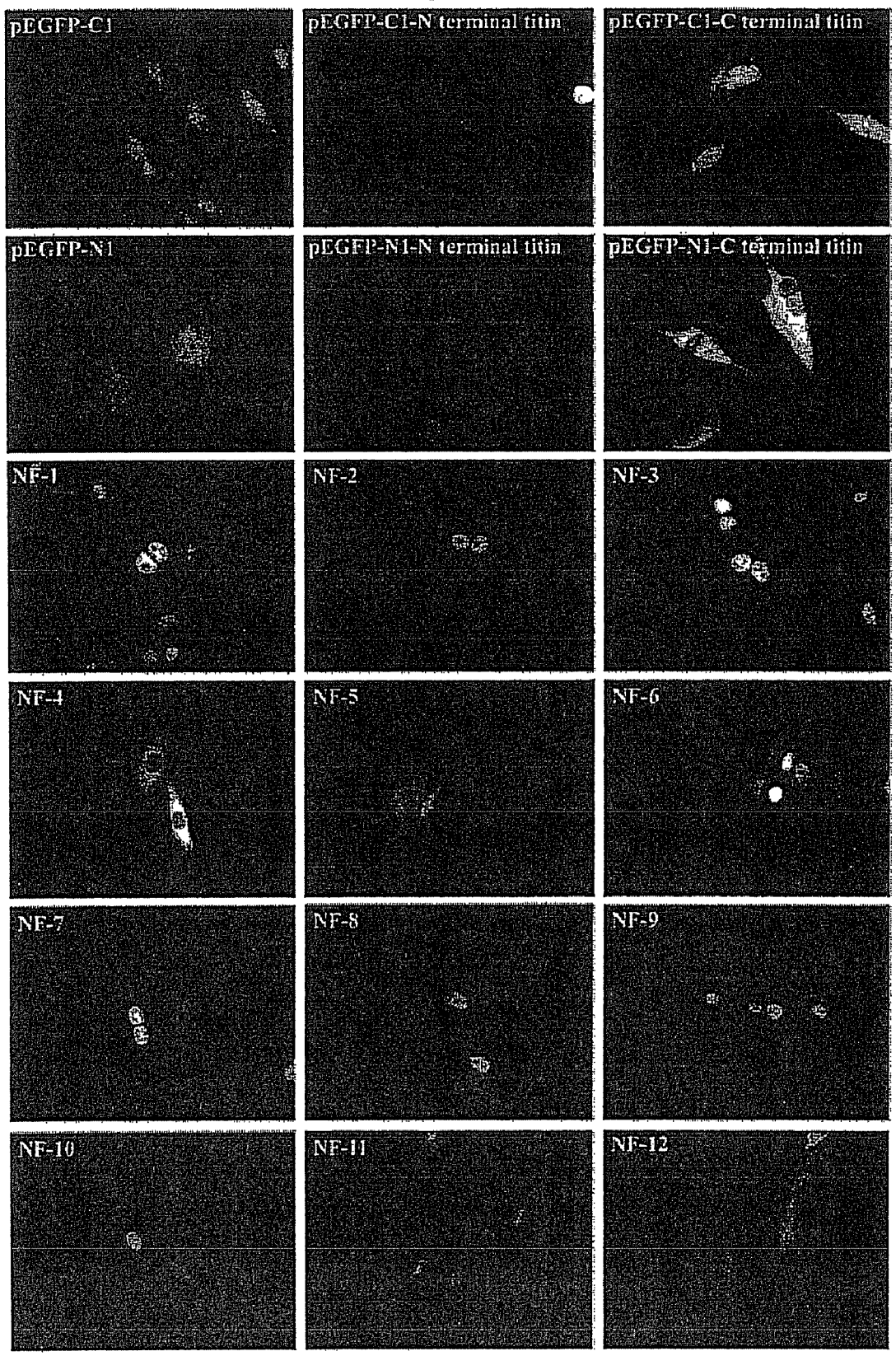
FIG. 5 illustrates localization of subclones of human titin N-termini in MG63 cells.

Only one potential NLS sequence was predicted by the PSORT II program. However, it was thought that there may be other non-classic NLS sequences in the titin-specific region at the N-terminus of human titin protein and, moreover, other domains may affect the function of this NLS sequence. Thus, to investigate the potential NLS sequences within the N-terminus of titin, eleven constructs were made in the enhanced green fluorescence reporter systems: pEGFP-C1 and pEGFP-N1 (FIG. 4). These constructs were transiently expressed in COS-7 cells. EGFP alone, as a control, showed both cytoplasmic and nuclear localization. The titin C terminus linked to the N- or C-terminus of EGFP was distributed in both the cytoplasm and nucleus. The N terminus linked to the N- or C-terminus of EGFP showed only nuclear localization, which indicated that there might be potential nuclear localization signals within the N-terminus of titin. The intracellular localization of constructs NF 1-5 showed that a potential NLS sequence localized between residues 180 and 209. Further deletion of residues in constructs NF 6-11 minimized the NLS sequence to a seven amino acid sequence: residues 200 to 206. The deletion of residues proline and alanine almost ablated the NLS function. These constructs also were transfected into MG63 cells and the stable transfectants for each construct were selected, in which the results were the same as what was observed in COS-7 cells (FIG. 5).

Nuclear Export Signal (NES) Sequences in Human Titin

A total of six potential NES sequences were predicted by the NetNES 1.1 program, as follows: 1705-FKKKLTSLR L-1714 (NES1) (SEQ ID NO: 16) in the N-terminus; the NES localized in Z repeats at the boundary of low complexity and an Ig domain; 1077-MALMLIV-1083 (NES2) (SEQ ID NO: 17) in Novex I, which localized within an Ig domain; both 3900-IKKDDLRELGL-3910 (NES3) (SEQ ID NO: 18) and 4712-LDILKTDLSL-4721 (NES4) (SEQ ID NO: 19) in Novex III localized in the extended region between Ig domains within a titin-specific sequence; 8923-LTTKEIKLE L-8932 (NES5) (SEQ ID NO: 20) localized to a low complexity, titin-specific sequence at the carboxy terminus of N2A; and 33040-LRLEEELEL-33048 (NES6) (SEQ ID NO: 21) localized in the low complexity, titin-specific sequence between M3 and M4 domains. (The conserved hydrophobic residues are underlined). The most important properties of the NES sequences have been shown to be accessibility and flexibility, which allow for receptor proteins to interact with the signals (La Cour et al., Protein Eng. Des. Sel., 17:527-536, 2004). Therefore, NES sequences 1 and 2 are less likely to be functional NES sequences.

Discussion

Titin is a giant filamentous protein, highly expressed in striated muscle tissues (the third most highly expressed protein after actin and myosin in muscle), mainly composed of Ig, Fn III and PEVK repeats. Titin plays an important role in the assembly of the sarcomere and contributes to the elasticity of muscle tissues. A deficiency in titin protein results in severe heart or skeletal muscle diseases. Hence, titin is an important architectural and regulatory protein. However, the functions of the titin-specific sequences at the amino and carboxyl termini of titin have not been explored. It has been argued that titin is found principally in the cytoplasm bound with myosin. Recent studies, however, indicate that titin may not only appear in the cytoplasm but also in the nucleus (Machado, C. et al., J. Cell Biol., 151:639-652, 2000). Nuclear titin may play important roles in regulating chromosome condensation and spindle organization (Wernyj, R. et al., Cell Motil. Cytoskeleton, 50:101-113, 2001). Due to its huge size, it is not feasible to determine its nuclear localization by heterogeneous expression of the whole protein. Analysis of the complete sequence of human titin revealed that there are several titin-specific sequence insertions at both the N- and C-termini (Bang, M. et al., Circ. Res., 89:1065-1072, 2001). However, there is no report of potential NLS sequences in human titin. This investigation constructed and transiently expressed GFP-titin fusion proteins of N- and C-terminal fragments in several mammalian cell lines and, for the first time, demonstrated that there is a functional NLS within the titin-specific region at the amino terminus of human titin, which indirectly supports the finding that titin occurs in the nucleus. When P-A residues are deleted, the NLS is disrupted. The results from this study suggest that a proline residue may be important for maintaining the accessibility and flexibility of the NLS so that the signals may be accessible to the receptor proteins.

The mechanism for regulating the importation of classic NLS-containing nuclear proteins has been well investigated (Adam, S. et al., Cell, 66:837-847, 1991; Gorlich, D., EMBO J., 17:2721-2727, 1998; Imamoto, N. et al., EMBO J., 14:3617-3626, 1995; Moroianu, J. et al., Proc. Natl. Acad. Sci. USA, 92:2008-2011, 1995). The first step is the reorganization of NLS sequences by importin α. This step can be regulated by the blockage of NLS sequences by mask domains or partner proteins. Because titin is a filamentous protein and the NLS sequence(s) locates outside of Ig domains, it is likely that this step may be regulated by titin-binding proteins. Many titin N-terminus-binding proteins have been reported, such as T-cap, obscuring, α-actinin and telethonin (Gregorio, C. et al., Curr. Opin. Cell Biol., 11:18-25, 1999; McElhinny, A. et al., J. Cell Biol., 157:125-136, 2002; Pyle, W. G. et al., Circ. Res., 94:296-305, 2004; Sanger J. et al., J. Cell Biol., 154:21-24, 2001). The potential regulators for the importation of titin into the nucleus may be among them.

NES sequences were found in most of the shuttle proteins which can be transported into and exported out of the nucleus, such as actin, NF-κB, NF-AT and hnRNP (Harhaj, E. et al., Mol. Cell. Biol., 19:7088-7095, 1999; Michael, W. et al., EMBO J, 16:3587-3598, 1997; Wada, A. et al., EMBO J, 17:1635-1641, 1998; Zhu, J. et al., Nature, 398:256-260, 1999). Because titin appears to be transported to the nucleus as a potential shuttle protein, then there also may be NES sequences in titin. As expected, several NES sequences were predicted in the N-terminus: Novex I and III, N2A; and in the C-terminus by the program NetNES 1.1 (La Cour et al., Protein Eng. Des. Sel., 17:527-536, 2004). Many of the reported shuttle proteins are known to be involved in signal transduction/gene regulation and cell cycle regulation, which suggest that titin may play multiple roles other than only as an elastic protein. It has been shown that the kinase domain of titin regulates the expression of muscle genes (Lange, S. et al., Science, 308:1599-1603, 2005).

In conclusion, the results from this investigation indicate that titin appears to be a shuttle protein which is localized both in the cytoplasm and in the nucleus of cells. Thus, titin not only plays a cytoskeletal role but also apparently participates in the regulation of gene transcription and mitosis by regulating chromosomal configuration and spindle contraction in the nucleus.

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

TABLE 1

Primers for making the NLS-localizing constructs in pEGFP-C1

| Clone | Forward (5' to 3') | Reverse (5' to 3') |
|---|---|---|
| NF-1 | AAAACTCGAGCTATGACAACTCAA GCA CCG ACG TTT | AAAAGGATCCAACTTCATT ATTGCTTCTTGAGT TAC |
| NF-2 | AAAACTCGAGCTATGACAACTCAA GCA CCG ACG TTT | AAAAGGATCCAAAGTAATT TCTTCAGAAATTCTAGT |
| NF-3 | AAAACTCGAGCTATGACAACTCAA GCA CCG ACG TTT | AAAAGGATCCAATCGGGTT TGTCTTGATTCTGAGAT |
| NF-4 | AAAACTCGAGCTATGACAACTCAA GCA CCG ACG TTT | AAAAGGATCCAAATTGGTG GCATTTACTGAATAGGT |
| NF-5 | AAAACTCGAGCTTCGACTGCTCAG ATC TCA GAA | AAAAGGATCCAACTGTGAT GATATGTGCATTCCCTT |
| NF-6 | AAAACTCGAGCTGGCCGCGCTAAA CTG ACG ATC | AAAAGGATCCAATCGGGTT TGTCTTGATTCTGAGAT |
| NF-7 | AAAACTCGAGCTGTGAGACTCCAA GTG AGA GTG ACT | AAAAGGATCCAATCGGGTT TGTCTTGATTCTGAGAT |
| NF-8 | AAAACTCGAGCTAGCGTTGGAAGA GCT ACT TCG ACT | AAAAGGATCCAATCGGGTT TGTCTTGATTCTGAGAT |
| NF-9 | TCCGCTAGCGCTACCGGTCGCCAC | AAAAAGCTTTTAAACAATT GTCTTTGTCTTTTTAGCAG GTACTTCTTCTTCACCTTG AACCTTGTACAGCTCGTCC ATGCCGA |
| NF-10 | TCCGCTAGCGCTACCGGTCGCCAC | AAAAAGCTTTTAAACAATT GTCTTTGTCTTTTTAGCAG GTACCTTGTACAGCTCGTC CATGCC GA |
| NF-11 | TCCGCTAGCGCTACCGGTCGCCAC | AAAAAGCTTTTATGTCTTT GTCTTTTTAGCAGGGCTGT ACAGCTCGTCCATGCCGA |
| NF-12 | TCCGCTAGCGCTACCGGTCGCCAC | AAAAAGCTTTTATGTCTTT GTCTTTTTGCTGTACAGCT CGTCCATGCCGA |

Note:
The C-terminal residue of EGFP was mutated from lysine to serine (AAG to AGC) in NFs 11-12.

TABLE 2

Prediction of Nuclear Export Signals (NES) in Human Titin.

| Domains | Predicted NES |
|---|---|
| N-terminus | 1705-FKKKLTSLRL-1714 |
| Novex I | 1077-MALMLIV-1083 |
| Novex II | None |
| Novex III | 3900-IKKDDLRELGL-3910 |
|  | 4712-LDILKTDLSL-4721 |
| N2B | None |
| N2A | 8923-LTTKEIKLEL-8932 |
| C-terminus | 33040-LRLEEELEL-33048 |

Note:
The amino acid residue numbers were from the Genbank entries as follows: N-terminus (CAD12456), Novex I (CAD12459.1), Novex II (CAD12458.1), Novex III (NP_596870.1), N2B (CAD12455), N2A (NP_596869) and C-terminus (CAD12456). The conserved hydrophobic residues were underlined.

---

The invention claimed is:

1. A method for transporting a target protein into the nucleus of a cell in vitro, comprising introducing into a cell a composition comprising a nuclear localization signaling (NLS) sequence consisting of the amino acid sequence of SEQ ID NO: 1 or a fragment of SEQ ID NO: 1 comprising SEQ ID NO: 4, wherein said NLS sequence is linked to an agent in order to transport the agent into the nucleus of the cell.

2. The method according to claim 1, wherein said agent is linked to an antibody or ligand to form an NLS-agent-antibody or NLS-agent-ligand complex, in which said complex recognizes a specific cell surface-expressing antigen or receptor, respectively, on the cell in order to enter the cytoplasm of the cell before being transported into the nucleus of the cell.

3. The method according to claim 1, wherein said agent is comprised of one or more peptides, proteins or nucleic acids.

4. The method of claim 1, wherein said agent is a nucleic acid sequence for the target protein to form a NLS-nucleic acid construct.

5. The method according to claim 1, wherein said fragment of SEQ ID NO: 1 is selected from the group consisting of SEQ ID NO: 2 and SEQ ID NO: 3.

6. The method according to claim 1, wherein the cell is a mammalian cell.

7. The nuclear method according to claim 6, wherein the mammalian cell is a human cell.

* * * * *